United States Patent
Kuwano et al.

(10) Patent No.: US 7,455,855 B2
(45) Date of Patent: Nov. 25, 2008

(54) DELIVERING SUBSTANCE AND DRUG DELIVERY SYSTEM USING THE SAME

(75) Inventors: Mitsuaki Kuwano, Ikoma (JP); Masaki Nakagawa, Ikoma (JP); Hiroshi Suhara, Osaka (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 443 days.

(21) Appl. No.: 10/240,438

(22) PCT Filed: Apr. 3, 2001

(86) PCT No.: PCT/JP01/02882

§ 371 (c)(1),
(2), (4) Date: Sep. 30, 2002

(87) PCT Pub. No.: WO01/74400

PCT Pub. Date: Oct. 11, 2001

(65) Prior Publication Data

US 2003/0144247 A1    Jul. 31, 2003

(30) Foreign Application Priority Data

Apr. 3, 2000 (JP) ............................ 2000-101113
Mar. 1, 2001 (JP) ............................ 2001-56912

(51) Int. Cl.
*A61F 2/00* (2006.01)
(52) U.S. Cl. ........................ 424/427; 424/428; 514/78
(58) Field of Classification Search ................ 424/450, 424/427, 422, 428; 514/169, 11, 263.1, 254.11, 514/460, 588
See application file for complete search history.

(56) References Cited

U.S. PATENT DOCUMENTS 4,179,337 A * 12/1979 Davis et al. ................. 435/181
4,804,539 A *  2/1989 Guo et al. ................... 424/450
5,308,624 A    5/1994 Maincent et al.

(Continued)

FOREIGN PATENT DOCUMENTS

EP    0 657 463 A1    6/1995

(Continued)

OTHER PUBLICATIONS

S.M. Foroutan et al., "The in vitro evaluation of polyethylene glycol esters of hydrocortisone 21-succinate as ocular prodrugs," *Intl. Journal of Pharma.*, vol. 182, pp. 79 to 92 (1999).

(Continued)

*Primary Examiner*—Gollamudi Kishore
(74) *Attorney, Agent, or Firm*—Frishauf, Holtz, Goodman & Chick, P.C.

(57) ABSTRACT

An object of the present invention is to prepare substances which are excellent in delivery and enable drugs to be retained in a body effectively over a long period and to construct a drug delivery system using the substances. When the delivering substance which is obtained by reacting polyalkylene glycol or a reactive derivative thereof, a phospholipid and a drug with each other to form covalent bonds is administered systemically or topically, the substance is retained at a target site in a body for a long period, thereby making it possible to sustain drug efficacy over a long period by a single administration.

12 Claims, 2 Drawing Sheets

U.S. PATENT DOCUMENTS

| | | | |
|---|---|---|---|
| 5,411,947 A * | 5/1995 | Hostetler et al. ............... 514/43 |
| 6,060,463 A | 5/2000 | Freeman | |
| 6,171,614 B1 * | 1/2001 | Chaikof et al. ............... 424/450 |
| 6,204,054 B1 * | 3/2001 | Sutton et al. ................ 435/334 |
| 6,258,351 B1 * | 7/2001 | Harris ....................... 424/78.3 |
| 6,602,498 B2 * | 8/2003 | Shen ....................... 424/78.08 |
| 2002/0064520 A1 * | 5/2002 | Rozenberg et al. ......... 424/93.2 |
| 2003/0191098 A1 | 10/2003 | D'Amato | |
| 2004/0254197 A1 | 12/2004 | Tasaka et al. | |

FOREIGN PATENT DOCUMENTS

| | | |
|---|---|---|
| JP | 4-221322 A | 8/1992 |
| JP | 6-508369 A | 9/1994 |
| JP | 8-117586 A | 5/1996 |
| WO | 93/00076 A1 | 1/1993 |
| WO | WO 93/24476 A1 | 12/1993 |
| WO | WO 97/19694 A1 | 6/1997 |
| WO | WO 99/39732 A1 | 8/1999 |
| WO | WO 99/48535 A1 | 9/1999 |
| WO | WO 00/07629 A2 | 2/2000 |
| WO | WO 00/35422 A2 | 6/2000 |
| WO | WO 00/45835 A1 | 8/2000 |
| WO | WO 00/64483 A2 | 11/2000 |
| WO | WO 01/51003 A2 | 7/2001 |
| WO | WO 01/74400 A1 | 10/2001 |
| WO | 03/053452 * | 7/2003 |

OTHER PUBLICATIONS

M.E. Szabo et al., "Ischemia and Reperfusion-Induced Histologic Changes in the Rat Retina," *Invest. Ophthal. & Visual Sci.*, vol. 32, No. 5, pp. 1471 to 1478 (1991).

Daniel W. Drolet et al., "Pharmacokinetics and Safety of an Anti-Vascular Endothelial Growth Factor Aptamer (NX1838) Following Injection into the Vitreous Humor of Rhesus Monkeys," *Pharmaceutical Research*, vol. 17, No. 12, (2000), pp. 1503-1510.

The Eyetech Study Group, "Preclinical and Phase 1A Clinical Evaluation of an Anti-VEGF Pegylated Aptamer (Eye001) for the Treatment of Exudative Age-Related Macular Degeneration," *Retina*, vol. 22, No. 2, (2002), pp. 143-151.

Sorbera et al., "Pegaptanib Sodium: Treatment of Age-Related Macular Degeneration Treatment of Diabetic Retinopathy Anti-VEGF Aptamer," *Drugs of the Future*, vol. 27, No. 9, (2002), pp. 841-845.

* cited by examiner

DELIVERING SUBSTANCE AND DRUG DELIVERY SYSTEM USING THE SAME

This application is a U.S. National Phase Application under 35 U.S.C. 371 of International Application No. PCT/JP01/02882 filed Apr. 3, 2001.

TECHNICAL FIELD

The present invention relates to substances being excellent in delivery which are obtained reacting polyalkylene glycol or a reactive derivative thereof, a phospholipid and a drug with each other to form covalent bonds and to a drug delivery system which makes it possible to retain the drug at a specific site of a body for a long period by administering the delivering substance systemically or topically.

BACKGROUND ART

Intraocular diseases such as diseases of a retina, an optic nerve or a vitreous body are often intractable, and a development of an effective treatment method is eagerly desired. Though ocular diseases are most generally treated by instillation of drugs, the drugs are hardly delivered to the intraocular tissues such as a retina, rendering the treatment of the intraocular diseases all the more difficult.

In view of this, a method of administering a drug directly to a specific site of a body was attempted. For example, a technique for administering a liposome or a microsphere containing a drug to intraocular tissues such as a vitreous body was reported (Published Japanese Translation of PCT No. 508369/1994, Japanese Laid-open Patent Publication No. 221322/1992 and the like).

However, it is not easy to control release of the drug by using the liposome. The liposome and the microsphere have large particle diameters. Accordingly, when they are administered to the intraocular tissues such as the vitreous body, transparency in the vitreous body sometimes cannot be maintained.

On the other hand, when the drug is administered orally, the drug is easily absorbed and metabolized in a stomach, a small intestine, a large intestine, a liver. Accordingly, it is difficult to deliver the drug to a specific site to attain a concentration at which drug efficacy is exhibited.

From these facts, it is an important subject to prepare substances which are excellent in delivery and enable drugs to be retained in a body effectively over a long period and to create a drug delivery system using the substances.

DISCLOSURE OF THE INVENTION

Focusing attention on delivering substances and a drug delivery system using the delivering substances and studying them precisely, the present inventors prepared substances being excellent in delivery which are obtained by reacting polyalkylene glycol or a reactive derivative thereof, a phospholipid and a drug with each other to form covalent bonds. Thus, it was found that the delivering substances and a systemic or topical drug delivery system using the delivering substances can be used for treatment of diseases at various sites of a body. When the delivering substances are administered to the vitreous body, the delivering substances are retained in a retina and a vitreous body for a long period.

The present invention provides the delivering substances containing polyalkylene glycol or a reactive derivative thereof, the phospholipid and the drug linked by covalent bonds, and the drug delivery system to administer the substance systemically or topically. The present invention also provides a method of treatment comprising administering systemically or topically to a patient a pharmaceutically effective amount of the delivering substance containing polyalkylene glycol or the reactive derivative thereof, the phospholipid and the drug linked by the covalent bonds solely or combined with a pharmaceutically acceptable carrier or additive, and use of the substance.

When the delivering substance of the present invention is administered systemically or topically, the substance is retained at a target site in a body for a long period, thereby making it possible to sustain drug efficacy over a long period by a single administration.

The present invention relates to the delivering substances represented by the following general formula [1] and containing polyalkylene glycol or the reactive derivative thereof, the phospholipid and the drug linked by the covalent bonds,

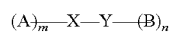

$$(A)_m\text{—}X\text{—}Y\text{—}(B)_n \quad [1]$$

wherein A and B, being the same or different, are residues of the drug, X is a residue of polyalkylene glycol or the reactive derivative thereof, Y is a phospholipid skeleton or a residue of the phospholipid, m is 0 or an integer of 1 or more, n is 0 or 1, at least one of m and n is not 0, and all of A, B, X and Y are linked by the covalent bonds, namely, "—" in the formula [1] stands for the covalent bond.

The polyalkylene glycol is a polymer containing a repeating unit [—O—alkylene—], and the alkylene can be substituted by lower alkyl or hydroxyl. Preferred examples of the polyalkylene glycol are polymers consisting of $C_{2-3}$ alkylene chains, and more preferred examples thereof are polyethylene glycol and polypropylene glycol. The reactive derivative of the polyalkylene glycol is a derivative having at least one chemically-modified terminal of the polyalkylene glycol so that the polyalkylene glycol can be linked to the drug or the phospholipid by the covalent bond. Preferred examples of the reactive derivative are derivatives having aminoalkyl, carboxyalkyl, mercaptoalkyl, hydrazidoalkyl, maleimidoalkyl, sulfonylalkyl, vinylsulfonylalkyl, vinylcarbonyl introduced into one or both of the terminals of the polyalkylene glycol. More preferred examples of the reactive derivative are derivatives having aminoethyl, aminopropyl, carboxymethyl, carboxyethyl, mercaptoethyl or hydrazidomethyl introduced into one or both of the terminals.

When m is zero in the general formula [1], a OH group located at one terminal of the polyalkylene glycol can be protected with alkyl, acyl or the like.

The polyalkylene glycol or the reactive derivative thereof can be any of straight-chain, stellate and branched and can appropriately be selected considering a concentration of the delivering substance at the target site, a period necessary for retaining the delivering substance at the target site, and the like. Plural drugs can be linked to one delivering substance by covalent bonds by using the stellate or branched polyalkylene glycol or the reactive derivative thereof.

As a bonding form, the drug, the polyalkylene glycol (including the reactive derivative thereof) and the phospholipid are preferably linked in the form of drug-polyalkylene glycol-phospholipid. They can also be linked in the form of polyalkylene glycol-phospholipid-drug or drug-polyalkylene glycol-phospholipid-drug.

The plural drugs can be linked to the polyalkylene glycol by selecting a suitable polyalkylene glycol. Further, the plural drugs can be linked to the delivering substance by linking the drug to the phospholipid.

A molecular weight of the polyalkylene glycol or the reactive derivative thereof constituting the delivering substance of the present invention is not limited and can appropriately be selected considering a drug delivery site of a body, the kind and properties of the drug forming the covalent bond, a required concentration of the delivering substance, a period for retaining the delivering substance, and the like. The molecular weight is usually 500 to 200,000, more preferably 1,000 to 50,000.

Chemical structure of the drug linked to the polyalkylene glycol or the reactive derivative thereof by the covalent bond is not limited, and the drug can have a functional group which can be linked to the polyalkylene glycol or the reactive derivative thereof. Preferred examples of the drug are ones having hydroxyl, carboxyl, carbonyl, amino, alkenyl. The kind of the drugs is not limited so far as the drugs are systemic or topical ones having therapeutic effects or preventive effects on various diseases. Examples of the drugs are anti-inflammatories, immunosuppressors, antivirals, antimicrobials, antimycotics, antitumors, nerve-protecting drugs, bloodflow-improving drugs, antiglaucomatous drugs, analgesics, anesthetics, angiogenesis inhibitors, diagnostic agents. Examples of drugs to be used for treatment or prevention of diseases of a retina, an optic nerve, a vitreous body are drugs which are effective for intraocular inflammation due to various causes, viral or bacterial infections, proliferative viteoretinopathy accompanied by proliferation of retinal cells, retinal neovasculaturigation, retinal hemorrhage due to various causes, retinal detachment or retinoblastoma. For example, anti-inflammatories such as betamethasone phosphate are used for treating inflammation accompanying an intraocular surgical operation. Immunosuppressors such as ciclosporin are used for treating autoimmune uveitis. Antivirals such as ganciclovir are used for treating viral infections. Antimicrobials such as ofloxacin are used for treating postoperative infections. Antitumors such as doxorubicin hydrochloride, carmustine, anti-VEGF and MMP inhibitors, ophthalmic diagnostic agents are used for treating proliferative viteoretinopathy.

In order to link the polyalkylene glycol or the reactive derivative thereof to the drug by the covalent bond, they can be chemically reacted each other, considering the functional group of the drug and the functional group of the polyalkylene glycol or the reactive derivative thereof. They can be linked by widely used methods. Though the polyalkylene glycol itself can form the covalent bond, the reactive derivative thereof can much easily form the covalent bonds with various drugs. Since reactive derivatives of polyalkylene glycol having various functional groups such as amino, thiol, carboxyl, succinimidylcarboxylate, epoxide, aldehyde, isocyanate, maleimide, acrylate and vinylsulfone are commercially available, the covalent bonds can be formed by chemically reacting these reactive derivatives with the drug having the functional group.

Examples of the covalent bond formed in the delivering substances are ester linkage, amide linkage, ether linkage, carbamate linkage, urea linkage, thiourea linkage, sulfide linkage, disulfide linkage, sulfone linkage, carbonate linkage, a carbon—carbon bond. Delivering substances having desired covalent bonds can be synthesized considering the functional group of the drug, the functional group of the polyalkylene glycol or the reactive derivative thereof, a functional group of the phospholipid, a retention period at a diseased site in a body.

The phospholipid linked to the polyalkylene glycol or the reactive derivative thereof by the covalent bond is not limited and is exemplified by compounds represented by the following general formula [2] or salts thereof,

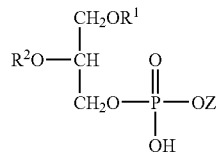

[2]

wherein $R^1$ and $R^2$, being the same or different, are hydrogen, alkyl, alkylcarbonyl, alkenyl or alkenylcarbonyl, and Z is aminoalkyl, diaminoalkyl, hydroxyalkyl or dihydroxyalkyl.

The phospholipid is not limited so far as the phospholipid has low toxicity and is excellent in safety. Examples of the phospholipid are soybean lecithin, egg yolk lecithin, phosphatidylethanolamine, phosphatidylglycerol, phosphatidic acid, synthetic lecithin. Examples of $R^1$ and $R^2$ in the compounds represented by the general formula [2] are alkylcarbonyl (alkanoyl) such as lauroyl, myristoyl, palmitoyl, stearoyl, oleoyl or linoleoyl, residues of the drugs. Examples of Z are aminoethyl, hydroxyethyl, 2,3-dihydroxypropyl.

The phospholipid preferably has a labile functional group in order to link the polyalkylene glycol or the reactive derivative thereof to the phospholipid by the covalent bond. The functional group of the phospholipid is not limited and is exemplified by functional groups having lability such as amino in phosphatidylethanolamine, hydroxyl in phosphatidylglycerol and carboxyl in phosphatidylserine. A particularly preferred phospholipid is phosphatidylethanolamine.

Examples of processes for linking the polyalkylene glycol or the reactive derivative thereof to the phospholipid by the covalent bond are a process using an acid anhydride, a process using cyanuric chloride, a process using carbodliimide, a process using glutaraldehyde. The best process can appropriately be selected among these processes to link a compound having the polyalkylene glycol or the reactive derivative thereof to the phospholipid by the covalent bond.

Chemical structure of the drug which can be linked to the phospholipid by the covalent bond is not limited, and the drug can have a functional group which can be linked to the phospholipid. Examples of the drug are the above-mentioned ones as the drugs linked to the polyalkylene glycol or the reactive derivative thereof by the covalent bond. The drug linked to the phospholipid by the covalent bond can be the same as or different from the drug linked to the polyalkylene glycol or the reactive derivative thereof by the covalent bond, and the drugs can appropriately be combined considering diseases, symptoms, drug efficacy and the like.

The delivering substances of the present invention can be prepared by various processes. For example, as shown by the following scheme, the compound [A] is reacted with N-hydroxysuccinimide in the presence of a condensing agent (for example, N,N'-dicyclohexylcarbodiimide) to give the active ester compound [B]. Next, the active ester moiety of the compound [B] is reacted with a phospholipid having amino to give the amide compound [C]. t-Butoxycarbonyl introduced as a protecting group of the amide compound [C] is removed under an acidic condition to convert the compound [C] into the amine compound [D]. This amine compound is reacted with an active carbonyl compound (for example, isothiocyanate) to give the delivering substance [E] of the present invention.

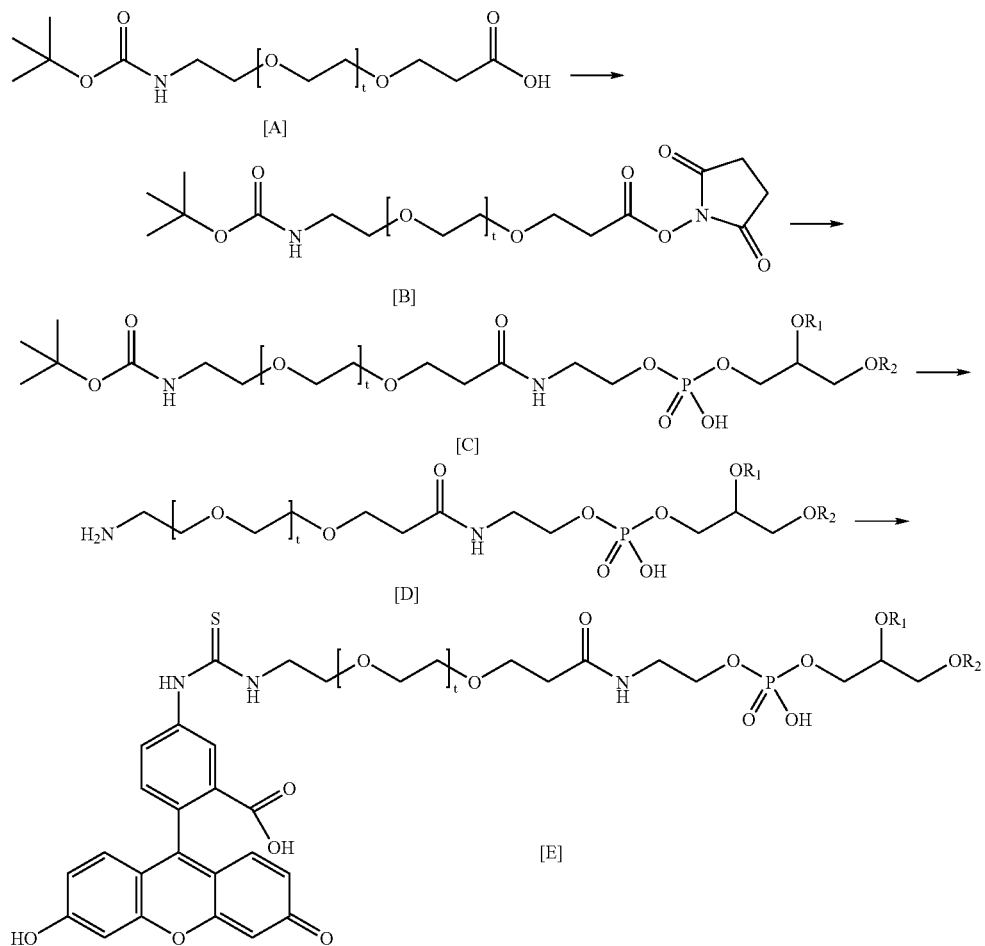

(wherein R[1] and R[2] have the same definitions as mentioned above, and t is an integer of 1 or more)

When the delivering substance of the present invention is administered systemically or topically, the delivering substance is retained at a specific site of a body and is hardly metabolized. Accordingly, the drug is released gradually at the site, thereby exhibiting therapeutic and preventive effects on diseases over a long period. The delivering substance per se retained at the specific site of the body can also exhibit therapeutic and preventive effects on the diseases. Accordingly, the drug delivery system of the present invention particularly makes it possible to treat the specific site of the body which has been difficult to treat so far, over a long period by a single administration.

The drug delivery system of the present invention can be used for treating or preventing various diseases at the specific site of the body by administering the delivering substance of the present invention systemically or topically. Specific examples of the disease are inflammation due to various causes, viral or bacterial infections, immunodeficiency, tumor, proliferative viteoretinopathy accompanied by proliferation of retinal cells, retinal neovasculaturigation, optic neuropathy, retinal hemorrhage, retinal detachment, retinoblastoma. Various diagnoses can be conducted by administering systemically or topically the delivering substance containing various diagnostic agents linked by covalent bonds.

It is preferable to adjust a drug content in the delivering substance to a content so as to maintain an actual concentration of the drug with the lapse of time.

Advantageous effects of the present invention are described in detail later in the section of the intraocular kinetic tests. Studying a delivering substance containing fluorescein linked by a covalent bond as a model drug for retentivity of the delivering substance in intraocular tissues (a vitreous body and a retina) after injection into the vitreous body, the delivering substance of the present invention was proved to be retained in not only the vitreous body but also the retina over a long period (56 days or more). Injecting Dizocilpine (drug) per se, which is reported to have an optic nerve-protecting action, and a delivering substance containing Dizocilpine linked by a covalent bond into vitreous bodies respectively and then comparing intraocular kinetics of the drug, it was elucidated that concentrations of the delivering substance of the present invention in the vitreous body, a retinochoroid and an optic nerve are 100 or more times higher than that in a case where Dizocilpine per se is used, and a disappearance half-life is also prolonged remarkably.

These test results show that various systemic or topical diseases can be treated effectively by selecting appropriately the drug linked by the covalent bonds to the polyalkylene glycol or the reactive derivative thereof and/or the phospholipid of the present invention with a fewer times of administration. When the drug delivery system of the present invention is used, the delivering substance can be retained efficiently at the specific site of the body such as the retina, the optic nerve or the vitreous body. Accordingly, it is possible to reduce an amount of the drug linked by the covalent bonds to the polyalkylene glycol or the reactive derivative thereof, the phospholipid, and an effect of reducing side-effects can also be exhibited.

Since the delivering substances of the present invention are retained efficiently at the specific site in a body, the substances are particularly effective for treating topical diseases. Their preparation forms are not limited and are exemplified by injections, infusions, tablets, ointments, emulsions, suspensions and the like. For example, various dosage forms and methods of administration such as eyedrops, injections, irrigations, iontophoresis and needleless injections can be used for ophthalmopathy. The delivering substances in the drug delivery system of the present invention can be formulated into preparation forms suited for methods of administration thereof (intraocular administration and the like) by widely used processes. For example, in the case of the injections, practical preparation examples thereof are described in Examples. The injections can be prepared by dissolving the delivering substance prepared by the above-mentioned process in BSS (Balanced Salt Solution), a glycerin solution, a hyaluronic acid solution. A stabilizer, an isotonic agent, a buffer, a pH adjustor, a preservative can optionally be added to the injections.

Examples of the stabilizer are edetic acid, disodium edetate. Examples of the isotonic agent are glycerin, propylene glycol, polyethylene glycol, sodium chloride, potassium chloride, sorbitol, mannitol. Examples of the buffer are citric acid, boric acid, sodium hydrogenphosphate, glacial acetic acid, trometamol, ε-aminocaproic acid. Examples of the pH adjustor are hydrochloric acid, citric acid, phosphoric acid, acetic acid, sodium hydroxide, potassium hydroxide, sodium carbonate, sodium hydrogencarbonate. Examples of the preservative are sorbic acid, potassium sorbate, benzalkonium chloride, benzethonium chloride, p-hydroxybenzoate esters, sodium benzoate, dibutylhydroxytoluene, chlorobutanol, chlorhexidine gluconate.

BEST MODE FOR CARRYING OUT THE INVENTION

Figure 1:
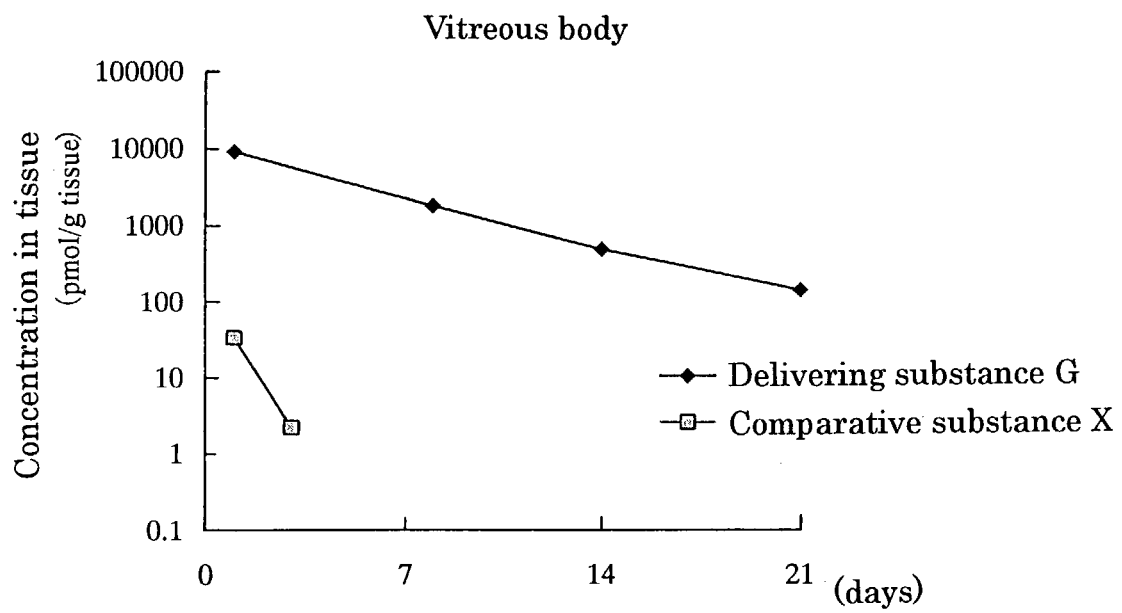
FIG. 1 is a graph showing changes of concentration with time (21 days) in vitreous body tissues.

Examples of the present invention are shown below, and they are intended for better understanding the present invention but are not to limit the scope of the present invention.

a. Preparation of Delivering Substances

Preparation Examples of delivering substances which can be used for a drug delivery system of the present invention are shown below.

EXAMPLE 1

(1) Delivering substance A, wherein
① a compound wherein hydrogen of one terminal OH group of polyethylene glycol (molecular weight: 5,000) is substituted by thioureidoethyl and hydrogen of the other terminal OH group is substituted by carbonylethyl,
② fluorescein and
③ L-α-distearoylphosphatidylethanolamine are linked by covalent bonds [chemical formula 6]

Methylene chloride (10 ml), chloroform (5 ml) and triethylamine (25 μl, 0.18 mmol) were added to a mixture of an active ester wherein hydrogen of one terminal OH group of polyethylene glycol (molecular weight: 5,000) was substituted by fluoresceinylthioureidoethyl and hydrogen of the other terminal OH group was substituted by succinimidyloxycarbonylethyl (Fluor-NHS-5k) [produced by Nippon Oils & Fats Co., Ltd.] (0.20 g, ca. 40 μmol) and L-α-distearoylphosphatidylethanolamine (61 mg, 82 μmol), and the whole was stirred at room temperature overnight. Then, p-toluenesulfonic acid (40 mg, 0.21 mmol) was added to the reaction mixture, and the whole was concentrated under reduced pressure. 2-Propanol was added to the concentrate, and the whole was stirred at room temperature for 30 minutes. Then, precipitated crystals were filtered off, methanol (10 ml) was added to the crystals, and an insoluble matter was filtered out. The filtrate was concentrated under reduced pressure, 2-propanol was added to the residue, and a precipitate was filtered off to give 151 mg of the delivering substance A as orange crystals.

mp: 56.5-64.5° C.

IR (KBr,cm $^{-1}$): 2886, 1741, 1611, 1468, 1344

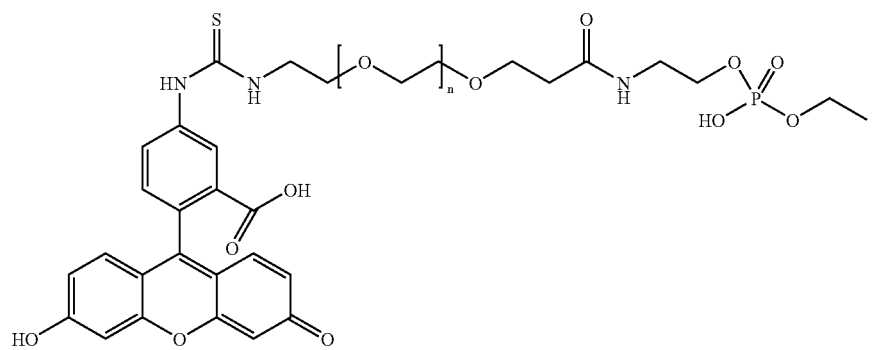

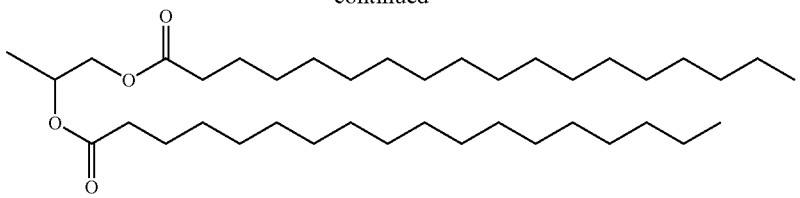

(2) Delivering substance B, wherein
① a compound wherein hydrogen of one terminal OH group of polyethylene glycol (molecular weight: 5,000) is substituted by thioureidoethyl and hydrogen of the other terminal OH group is substituted by carbonylethyl,
② fluorescein and
③ L-α-dioleoylphosphatidylethanolamine are linked by covalent bonds
mp: 49.0-51.0° C.
IR (KBr,cm$^{-1}$): 2889, 1741, 1613, 1468, 1344

(3) Delivering substance C, wherein
① a compound wherein hydrogen of one terminal OH group of polyethylene glycol (molecular weight: 1,000) is substituted by thioureidoethyl and hydrogen of the other terminal OH group is substituted by carbonylethyl,
② fluorescein and
③ L-α-distearoylphosphatidylethanolamine are linked by covalent bonds
mp: 55.0-65.0° C.
IR (KBr,cm $^{-1}$): 3313, 2917, 2850, 1748, 1617, 1540, 1468, 1349

(4) Delivering substance D, wherein
① a compound wherein hydrogen of one terminal OH group of polyethylene glycol (molecular weight: 10,000) is substituted by thioureidoethyl and hydrogen of the other terminal OH group is substituted by carbonylethyl,
② fluorescein and
③ L-α-distearoylphosphatidylethanolamine are linked by covalent bonds
mp: 55.0-60.0° C.
IR (KBr,cm$^{-1}$): 2885, 1745, 1614, 1468, 1343

(5) Delivering substance E, wherein
① a compound wherein hydrogen of one terminal OH group of polyethylene glycol (molecular weight: 5,000) is substituted by thioureidoethyl and hydrogen of the other terminal OH group is substituted by carbonylethyl,
② fluorescein and
③ L-α-dimyristoylphosphatidylethanolamine are linked by covalent bonds
mp: 65.0-75.0° C.
IR (KBr,cm $^{-1}$): 2886, 1774, 1618, 1467, 1344

EXAMPLE 2

Delivering Substance F, wherein
① a compound wherein hydrogen of both terminal OH groups of polyethylene glycol (molecular weight: 5,000) is substituted by carbonylethyl,
② (±) -3,4-dihydro-2-[5-methoxy-2-[3-[2-(3,4-methylenedioxy)phenoxyethyl-amino]propoxy]phenyl]-4-methyl-3-oxo-2H-1,4-benzothiazine and
③ L-α-distearoylphosphatidylethanolamine are linked by covalent bonds [chemical formula 7]

Chloroform (5 ml) was added to (±)-3,4-dihydro-2-[5-methoxy-2-[3-[2-(3,4-methylenedioxy)phenoxyethylamino] propoxy]phenyl]-4-methyl-3-oxo-2H-1,4-benzothiazine monooxalate [a process for preparing this compound is disclosed Japanese Laid-open Patent Publication No. 123181/1987.] (54 mg, 88 μmol), and the obtained mixture was stirred at room temperature. To the mixture were added triethylamine (0.04 ml, 0.3 mmol) and then an active ester wherein hydrogen of one terminal OH group of polyethylene glycol (molecular weight: 5,000) was substituted by L-α-distearoylphosphatidyloxyethylaminocarbonylethyl and hydrogen of the other terminal OH group was substituted by succinimidyloxycarbonylethyl (DSPE-NHS-5000) [produced by Nippon Oils & Fats Co., Ltd.] (0.30 g, ca. 50 μmol). After one hour, p-toluenesulfonic acid monohydrate (0.20 g, 1.1 mmol) was added to the reaction mixture, and the whole was concentrated under reduced pressure. 2-Propanol (20 ml) was added to the residue, the whole was stirred at room temperature for 15 minutes, and then an insoluble matter was filtered off to give 0.28 g of the delivering substance F as colorless crystals.
mp: 51.7-56.1° C.
IR (KBr,cm$^{-1}$): 2887, 1742, 1467, 1113

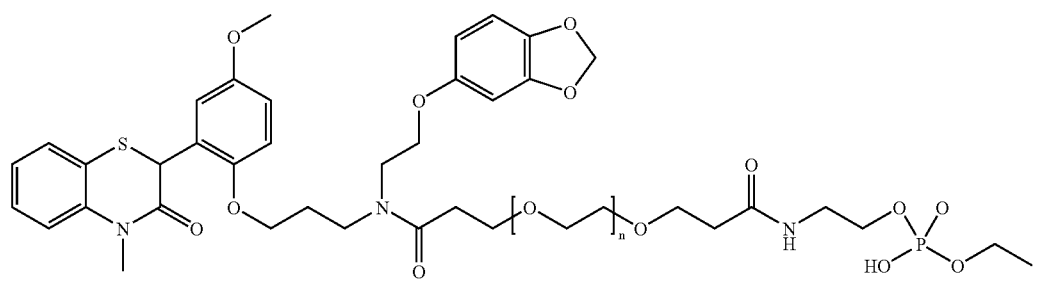

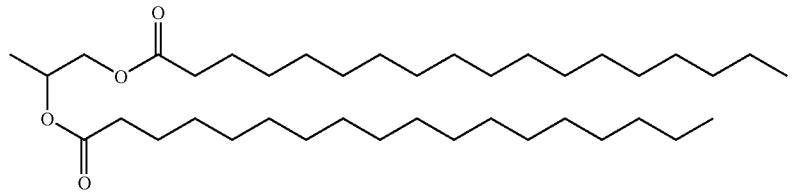

EXAMPLE 3

Delivering Substance G, wherein
① a compound wherein hydrogen of both terminal OH groups of polyethylene glycol (molecular weight: 5,000) is substituted by carbonylethyl,
② [5R, 10S]-(+)-5-methyl-10,11-dihydro-5H-dibenzo[a,d]cycloheptene-5,10-imine and
③ L-α-distearoylphosphatidylethanolamine are linked by covalent bonds [chemical formula 8]

Methylene chloride (6.4 ml) was added to [5R,10S]-(+)-5-methyl-10,11-dihydro-5H-dibenzo[a,d]cycloheptene-5,10-imine [Dizocilpine] maleate (0.12 g, 0.36 mmol) under a nitrogen atmosphere, and the obtained mixture was stirred at room temperature. To the mixture were added triethylamine (0.18 ml, 1.3 mmol) and then an active ester wherein hydrogen of one terminal OH group of polyethylene glycol (molecular weight: 5,000) was substituted by L-α-distearoylphosphatidyl-oxyethylaminocarbonylethyl and hydrogen of the other terminal OH group was substituted by succinimidyloxycarbonylethyl (DSPE-NHS-5000) [produced by Nippon Oils & Fats Co., Ltd.] (1.9 g, ca. 0.32 mmol), and the whole was stirred overnight. The reaction mixture was concentrated under reduced pressure, 0.1 N hydrochloric acid (100 ml) was added to the concentrate, and the whole was extracted with chloroform (100 ml) three times. The extract was dried over anhydrous sodium sulfate and concentrated under reduced pressure. The residue was purified by silica gel column chromatography, and the resulting crystals were filtered off to give 0.27 g of the delivering substance G as colorless crystals.

mp: 52.4-56.9° C.
IR (KBr,cm$^{-1}$): 3434, 2885, 1742, 1715, 1467, 1344, 1149, 1120 b. Formulation Examples (injection)

A sterilized 2.6% glycerin solution (10 ml) was added to the delivering substance G (30 mg), and the obtained mixture was warmed at 60° C. with stirring to give an injection in which the delivering substance G was dissolved. Desired injections can be obtained by changing appropriately the kind of the delivering substance of the present invention and the mixing ratio of the additive.

c. Intraocular Kinetic Tests by Fluorophotometry

Intraocular kinetic tests were conducted by the following methods using the delivering substances A and B containing a fluorescence.

Preparation of Delivering Substances:

Sterilized 2.6% glycerin solution (10 ml) was added to each of the delivering substances A and B (36 mg), and the obtained mixture was warmed to 60° C. with stirring to prepare an injection in which the delivering substance A was dissolved and an injection in which the delivering substance B was dissolved. The same procedure as mentioned above was repeated except that fluorescein sodium was used instead of the delivering substances A and B to prepare a 10 μg/ml injection containing fluorescein sodium for comparison.

Method of Administration and Method of Measurement:

1) A mixed solution containing an aqueous ketamine hydrochloride solution (50 mg/ml) and an aqueous xylazine hydrochloride (50 mg/ml) in a ratio of 7:3 was administered intramuscularly to white rabbits to anesthetize.

2) A tropicamide (0.5%)/phenylephrine hydrochloride (0.5%) ophthalmic solution was instilled into both eyes to cause mydriasis in the both eyes.

3) The both eyes were anesthetized with an oxybuprocaine hydrochloride (0.5%) ophthalmic solution.

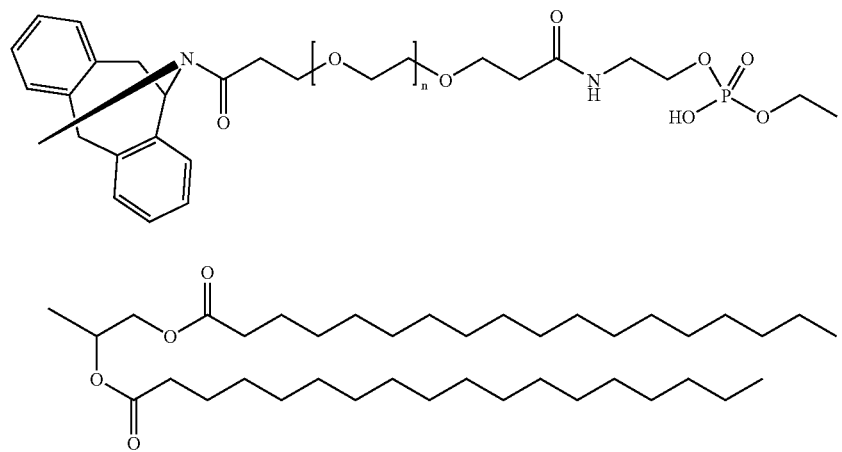

4) Each of the above-mentioned injection was administered to the center of a vitreous body from an ocular pars plana with a syringe equipped with a 30G needle.

5) Intraocular fluorescence intensity was measured with a fluorophotometry apparatus after the administration to the vitreous body at 1, 4, 7, 15, 35 and 56 days. A calibration curves were prepared, changes in concentration in the vitreous body and a retina were determined, and respective half-lives were calculated. The above-mentioned operations 1) and 2) were carried out before the intraocular fluorescence intensity was measured, too.

Results:

Table 1 shows half-lives of the delivering substances A and B and fluorescein sodium in the vitreous body, and Table 2 shows their half-lives in the retina. The numerical values in Tables 1 and 2 are the average of three samples respectively.

TABLE 1

| Test substance | Half-life (days) |
| --- | --- |
| Delivering substance A | 7.0 |
| Delivering substance B | 5.0 |
| Fluorescein sodium | <0.2 |

(The values in the table were calculated by a moment method from data measured 1 to 35 days after the injection into the vitreous body.)

TABLE 2

| Test substance | Half-life (days) |
| --- | --- |
| Delivering substance A | 19.5 |
| Delivering substance B | 16.5 |
| Fluorescein sodium | <0.1 |

(The values in the table were calculated by the moment method from data measured 1 to 56 days after the injection into the vitreous body.)

Consideration:

Table 1 explicitly shows that the half-lives of the delivering substances A and B in the vitreous body are 5.0 to 7.0 days, whereas that of fluorescein sodium is only less than five hours. These results show that the. delivering substances of the present invention prolong the retention period in the vitreous body remarkably. Table 2 explicitly shows that the half-lives of the delivering substances A and B in the retina are 16.5 to 19.5 days, whereas that of fluorescein sodium is only less than 2.4 hours. These results show that the delivering substances administered to the vitreous body migrate to the retina and are retained there for a long period.

d. Intraocular Kinetic Tests using Radioactive Isotopes

In order to study effects of the delivering substance G on retention in intraocular tissues (a vitreous body, a retina, an optic nerve and the like), intraocular kinetic tests using radioactive isotopes were conducted by the following methods.

Preparation of Drug Solutions:

The delivering substance G (9 mg) was weighed out and dissolved in a 2.6% aqueous glycerin solution in a 5 ml measuring flask to adjust a total amount to 5 ml. Into another test tube was introduced a 37 MBq/ml solution of a compound prepared by labeling the delivering substance G with tritium [$^3$H] (hereinafter referred to as "delivering substance G [$^3$H]") in toluene/ethanol (1:1) (200 μl), and toluene/ethanol was evaporated under a nitrogen stream. The delivering substance G solution (5 ml) prepared previously was added to this test tube, and the obtained mixture was stirred to prepare an administration solution.

On the other hand, [5R,10S]-(+)-5-methyl-10,11-dihydro-5H-dibenzo[a,d]cycloheptene-5,10-imine maleate (hereinafter referred to as "comparative substance X") (0.96 mg) was weighed out and dissolved in a 2.6% aqueous glycerin solution in a 10 ml measuring flask to adjust a total amount to 10 ml. Into another test tube was introduced a 37 MBq/ml solution of a compound prepared by labeling the comparative substance X with tritium [$^3$H] (hereinafter referred to as "comparative substance X [$^3$H]") in ethanol (400 μl), and ethanol was evaporated in a nitrogen stream. The comparative substance X solution (10 ml) prepared previously was added to this test tube, and the obtained mixture was stirred to prepare an administration solution. Sterilized instruments were used in all the preparation.

Injection into Vitreous Body:

A mixed solution containing an aqueous ketamine hydrochloride solution and an aqueous xylazine hydrochloride solution in a ratio of 7:3 was injected intramuscularly into Japanese white rabbits at a rate of 1 ml/kg to anesthetize the rabbits. Next, each surface of both eyes was anesthetized with an oxybuprocaine hydrochloride (0.5%) ophthalmic solution, and then the administration solution of each test substance (100 μl/eye) was injected into a vitreous body with a 30G needle. The injection was carried out with the needle equipped with a stopper so as not to introduce the needle into a retina. Table 3 shows concentrations, dosages of the respective administration solutions.

TABLE 3

| Adminstration solution | Concentration (μmol/ml) | Dosage (μl) | Administered radioactivity (KBq/eye) |
| --- | --- | --- | --- |
| Delivering substance G [$^3$H] | 0.300 | 100 | 148 |
| Comparative substance X [$^3$H] | 0.326 | 100 | 148 |

Collection of Samples:

Prescribed days after the administration, an aqueous sodium pentobarbital solution (50 mg/ml) (5 ml) was administered to ear veins of Japanese white rabbits to sacrifice. Eyeballs were washed with physiological saline (ca. 10 ml), then periphery of the eyeballs was cut from canthus or angulus oculi lateralis with a pair of scissors, and the eyeballs were enucleated. The eyeballs were washed with physiological saline twice, and excessive water was wiped off with paper. Each bulbar conjunctiva was removed, and then an aqueous humor (ca. 0.2 ml) was collected with a 1 ml syringe. Next, each eyeball was soaked in liquid nitrogen to freeze it, the eyeball was divided in two along its equator portion with a razor, a vitreous body, a crystalline lens, the iris and ciliary body, and a cornea were collected from an anterior portion, and a vitreous body, retinochoroid and an optic nerve were collected from a posterior portion.

Preparation of Samples for Measurement:

Wet weights of the collected vitreous body, retinochoroid and optic nerve were measured. After the measurement, they were dissolved with a tissue-dissolving agent, and then to the obtained solution was added a liquid scintillator.

Preparation of Standard Radioactive Samples:

The delivering substance G [$^3$H] administration solution and the comparative substance X [$^3$H] solution were diluted 1,000 times respectively to prepare standard radioactive samples.

Method of Determination:

Radioactivity concentrations of the prepared samples for measurement and standard radioactive samples were measured with a liquid scintillation counter. Radioactivity A per 1 ng of the test compound (dpm/pmol) was determined from radioactivity of each standard radioactive sample, and a radioactivity concentration in each tissue was calculated by the following equation.

Radioactivity concentration in tissue (pmol eq./g)=[{radioactivity in each tissue sample (dpm)}/A (dpm/pmol)]{wet weight of tissue (g)}

Calculation of Pharmacokinetic Parameters:

An elimination half-life was calculated by the moment method from a change in concentration of each test substance in the intraocular tissue measured 1 to 21 days after the injection into the vitreous body.

Figure 2:
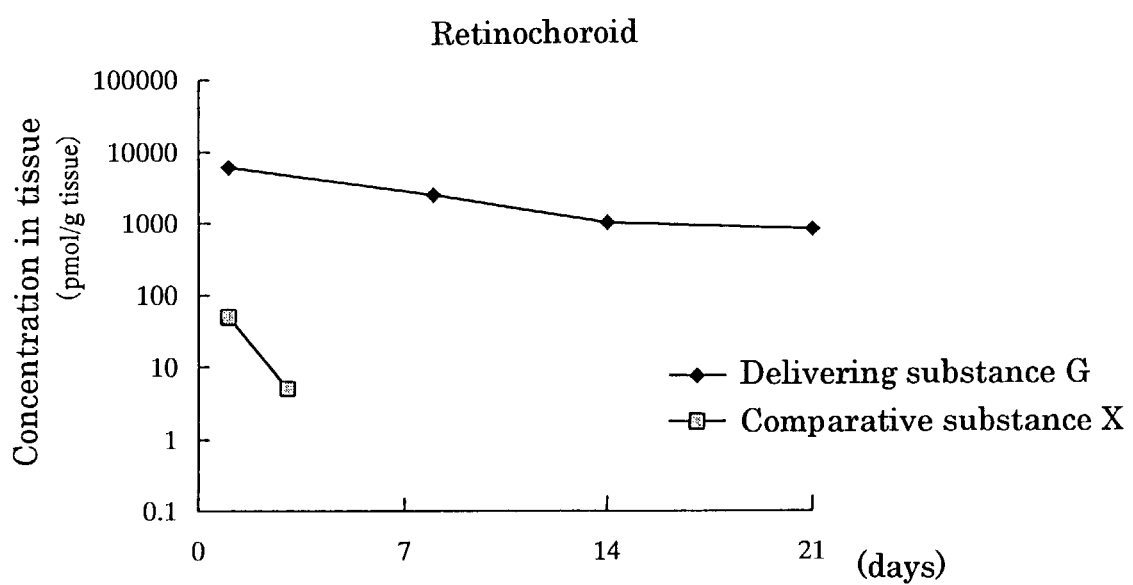
FIG. 2 is a graph showing changes of concentration with time (21 days) in retinochoroid tissues.
Figure 3:
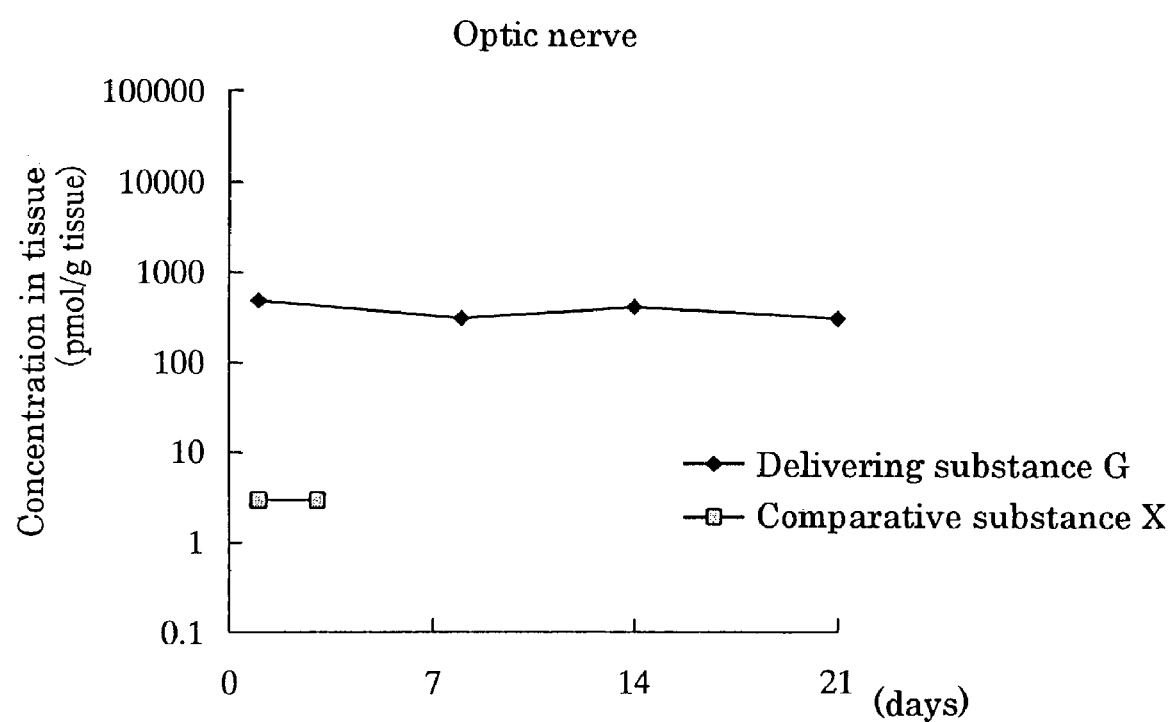
FIG. 3 is a graph showing changes of concentration with time (21 days) in optic nerve tissues.

Results:

FIGS. 1, 2 and 3 show respective changes in concentration of the delivering substance G and the comparative substance X in the vitreous body, the retinochoroid and the optic nerve after the injection into the vitreous body respectively. Tables 4 and 5 show half-lives of the delivering substance G and the comparative substance X in the vitreous body and a retina respectively. The numerical values in Tables 4 and 5 are the average of three samples respectively.

TABLE 4

| Test substance | Half-life (days) |
|---|---|
| Delivering substance G | 3.3 |
| Comparative substance X | 0.5 |

TABLE 5

| Test substance | Half-life (days) |
|---|---|
| Delivering substance G | 7.0 |
| Comparative substance X | 0.6 |

Consideration:

FIGS. 1 to 3 explicitly show that when the delivering substance G is administered to the vitreous body, the delivering substance migrates to posterior segments such as the vitreous body, the retinochoroid and the optic nerve and is retained at a high concentration over a long period. Tables 4 and 5 show that the half-life of the delivering substance is about 6 to 10 times longer than that of the comparative substance X.

The delivering substances of the present invention are substances being excellent in delivery which are obtained by reacting polyalkylene glycol or a reactive derivative thereof, a phospholipid and a drug with each other to form covalent bonds. The drug delivery system using the delivering substances of the present invention can retain the delivering substances in the posterior segments such as the vitreous body, the retina and the optic nerve for a long period. Accordingly, the drug delivery system for administering the delivering substances systemically or topically makes it possible to treat or prevent various diseases at specific sites of a body over a long period by a single administration.

INDUSTRIAL APPLICABILITY

The present invention provides substances being excellent in delivery which are obtained by reacting polyalkylene glycol or a reactive derivative thereof, a phospholipid and a drug with each other to form covalent bonds, and a drug delivery system using the substances.

The invention claimed is:

1. A method of treating a disease of a retina, an optic nerve or a vitreous body comprising administering to an eye or eyes of a patient a pharmaceutically effective amount of a delivering substance represented by the following formula [1] consisting essentially of a polyalkylene glycol, a phospholipid and a drug linked by covalent bonds solely or combined with a pharmaceutically acceptable carrier or additive, $$(A)_{\overline{m}}-X-Y-(B)_n \qquad [1]$$

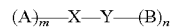

wherein A and B, being the same or different, are residues of the drug; X is polyalkylene glycol or a reactive derivative thereof having aminoalkyl, carboxyalkyl, mercaptoalkyl, hydrazidoalkyl, maleimidoalkyl, sulfonylalkyl, vinylsulfonylalkyl or vinylcarbonyl introduced into one or both terminals of the polyalkylene glycol, Y is a residue of the phospholipid, m is 0 or an integer of 1 or more, n is 0, 1 or 2, at least one of m and n is not 0, and all of A, B, X and Y are linked by the covalent bonds.

2. A method of treating a disease of a retina, an optic nerve or a vitreous body comprising instilling in an eye or eyes of a patient a pharmaceuticallY effective amount of a delivering substance represented by the following formula [1] consisting essentially of a polyalkylene glycol, a phospholipid and a drug linked by covalent bonds solely or combined with a pharmaceutically acceptable carrier or additive, $$(A)_{\overline{m}}-X-Y-(B)_n \qquad [1]$$

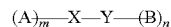

wherein A and B, being the same or different, are residues of the drug, X is polyalkylene glycol or a reactive derivative thereof having aminoalkyl, carboxyalkyl, mercaptoalkyl, hydrazidoalkyl, maleimidoalkyl, sulfonylalkyl, vinylsulfonylalkyl or vinylcarbonyl introduced into one or both terminals of the polyalkylene glycol, Y is a residue of the phospholipid, m is 0 or an integer of 1 or more, n is 0, 1 or 2, at least one of m and ri is not 0, and all of A, B, X and Y are linked by the covalent bonds.

3. A method of treating a disease of a vitreous body, a retina or an optic nerve comprising administering to the vitreous body of a patient a pharmaceutically effective amount of a delivering substance represented by the following formula [1] consisting essentially of a polyalkylene glycol, a phospholipid and a drug linked by covalent bonds solely or combined with a pharmaceutically acceptable carrier or additive, $$(A)_{\overline{m}}-X-Y-(B)_n \qquad [1]$$

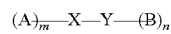

wherein A and B, being the same or different, are residues of the drug, X is polyalkylene glycol or a reactive derivative thereof having aminoalkyl, carboxyalkyl, mercaptoalkyl, hydrazidoalkyl, maleimidoalkyl, sulfonylalkyl, vinylsulfonylalkyl or vinylcarbonyl introduced into one or both terminals of the polyalkylene glycol, Y is a residue of the phospholipid, m is 0 or an integer of 1 or more, n is 0, 1 or 2, at least one of m and n is not 0, and all of A, B, X and Y are linked by the covalent bonds.

4. The method as claimed in claim 1, wherein the drug is an anti-inflammatory drug, an immunosuppressor, an antiviral drug, an antimicrobial drug, an antimycotic drug, an antitumor drug, a nerve-protecting drug, an ocular circulation improving drug, an antiglaucomatous drug, an analgesic, an anesthetic, an angiogenesis inhibitor or a diagnostic agent.

5. The method as claimed in claim 2, wherein the drug is a drug for treatment of a disease of a retina, an optic nerve or a vitreous body.

6. The method as claimed in claim 2, wherein the drug is an anti-inflammatory drug, an immunosuppressor, an antiviral drug, an antimicrobial drug, an antimycotic drug, an antitumor drug, a nerve-protecting drug, an ocular circulation improving drug, an antiglaucomatous drug, an analgesic, an anesthetic, an angiogenesis inhibitor or a diagnostic agent.

7. The method as claimed in claim 3, wherein the drug is an anti-inflammatory drug, an immunosuppressor, an antiviral drug, an antimicrobial drug, an antimycotic drug, an antitumor drug, a nerve-protecting drug, an ocular circulation improving drug, an antiglaucomatous drug, an analgesic, an aniogenesis inhibitor or a diagnostic agent.

8. The method as claimed in claim 2, wherein the drug is a drug for treatment of a disease of a retina, an optic nerve or a vitreous body.

9. The method as claimed in claim 3, wherein the drug is a drug for treatment of a disease of a retina, an optic nerve or a vitreous body.

10. The method as claimed in claim 1, wherein the drug is selected from the group consisting of betamethasone phosphate, ciclosporin, ganciclovir, ofloxacin, doxorubicin hydrochloride and carmustine.

11. The method as claimed in claim 2, wherein the drug is selected from the group consisting of betamethasone phosphate, ciclosporin, ganciclovir, ofloxacin, doxorubicin hydrochloride and carmustine.

12. The method as claimed in claim 3, wherein the drug is selected from the group consisting of betamethasone phosphate, caclosporin, ganciclovir, ofloxacin, doxorubicin hydrochloride and carmustine.

* * * * *